US011719054B2

(12) United States Patent
Al-Rubaii et al.

(10) Patent No.: US 11,719,054 B2
(45) Date of Patent: Aug. 8, 2023

(54) AUTOMATED DRILLING ADVISORY AND CONTROL SYSTEM

(71) Applicant: Saudi Arabian Oil Company, Dhahran (SA)

(72) Inventors: Mohammed Murif Al-Rubaii, Dammam (SA); Abdullah Saleh Hussain Al-Yami, Dhahran (SA); Salem H. Al Gharbi, Dammam (SA); Arturo Magana Mora, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 1034 days.

(21) Appl. No.: 16/421,107

(22) Filed: May 23, 2019

(65) Prior Publication Data

US 2020/0370381 A1 Nov. 26, 2020

(51) Int. Cl.
| | | |
|---|---|---|
| *E21B 21/08* | (2006.01) | |
| *E21B 44/06* | (2006.01) | |
| *E21B 45/00* | (2006.01) | |
| *E21B 47/08* | (2012.01) | |
| *G01N 33/28* | (2006.01) | |
| *E21B 21/00* | (2006.01) | |
| *E21B 44/00* | (2006.01) | |

(52) U.S. Cl.
CPC .............. *E21B 21/08* (2013.01); *E21B 21/00* (2013.01); *E21B 44/06* (2013.01); *E21B 45/00* (2013.01); *E21B 47/08* (2013.01); *G01N 33/2823* (2013.01); *E21B 44/00* (2013.01)

(58) Field of Classification Search
CPC .......... E21B 21/08; E21B 44/06; E21B 45/00; E21B 47/08; G01N 33/2823
See application file for complete search history.

(56) References Cited

U.S. PATENT DOCUMENTS

| | | |
|---|---|---|
| 2015/0129306 A1 | 5/2015 | Coffman et al. |
| 2015/0226049 A1 | 8/2015 | Frangos et al. |
| 2015/0300151 A1 | 10/2015 | Mohaghegh |

(Continued)

FOREIGN PATENT DOCUMENTS

| | | |
|---|---|---|
| EA | 013694 | 6/2010 |
| WO | 2011130159 | 10/2011 |
| WO | 2017027105 | 2/2017 |

OTHER PUBLICATIONS

Rubaii et al., A New Robust Approach for Hole Cleaning to Improve Rate of Penetration, Apr. 2018, Society of Petroleum Engineers, pp. 3-28 (Year: 2018).*

(Continued)

*Primary Examiner* — Lina Cordero
(74) *Attorney, Agent, or Firm* — Fish & Richardson P.C.

(57) ABSTRACT

Methods, systems, and computer-readable medium to perform operations including: obtaining, in real-time from one or more sensors of a drilling system, real-time drilling data of a drilling operation of drilling a wellbore; using the drilling data to calculate a carrying capacity index (CCI) of a drilling fluid and a cutting concentration in an annulus (CCA) of the wellbore; determining that at least one of the CCI and the CCA is outside a respective range; determining a corrective action to adjust the at least one of the CCI and the CCA to be within the respective range; and performing the corrective action.

13 Claims, 5 Drawing Sheets

(56) References Cited

U.S. PATENT DOCUMENTS

| | | | |
|---|---|---|---|
| 2016/0053604 A1* | 2/2016 | Abbassian | E21B 45/00 702/6 |
| 2016/0097270 A1 | 4/2016 | Pobedinski et al. | |
| 2017/0044896 A1* | 2/2017 | Salminen | E21B 49/003 |
| 2019/0316457 A1 | 10/2019 | Al-Rubaii et al. | |
| 2020/0371495 A1 | 11/2020 | Al-Rubaii et al. | |

OTHER PUBLICATIONS

Sifferman et al., Drill Cutting Transport in Full Scale Vertical Annuli, 1973, p. 2 (Year: 1973).*
Wastu et al., "The effect of drilling mud on hole cleaning in oil and gas industry," Journal of Physics: Conference Series, Dec. 2019, 1402(2), 7 pages.
PCT International Search Report and Written Opinion in International Appln. No. PCT/US2020/034215, dated Aug. 21, 2020, 15 pages.
Hopkin, "Factor Affecting Cuttings Removal during Rotary Drilling," Journal of Petroleum Technology 19.06, Jun. 1967, 8 pages.
Maurer, "The Perfect Cleaning Theory of Rotary Drilling," Journal of Petroleum Technology 14.11, 1962, 5 pages.
Rasi, "Hold Cleaning in Large, High-Angle Wellbores," SPE/IADC Drilling Conference, Society of Petroleum Engineers, Feb. 15-18, 1994, 12 pages.
Sifferman et al., "Drilling cutting transport in full scale vertical annuli," Journal of Petroleum Technology 26.11, 48th Annual Fall Meeting of the Society of Petroleum Engineers of AIME, Las Vegas, Sep. 30-Oct. 3, 1973, 12 pages.
Williams and Bruce, "Carrying Capacity of Drilling Muds," Journal of Petroleum Technology, 3.04, vol. 192, 1951, 10 pages.
"Hole Cleaning," Petrowiki, retrieved on Jan. 25, 2019, 8 pages.
Hopkin, "Factors Affecting Cuttings Removal during Rotary Drilling," Journal of Petroleum Technology, vol. 19, No. 6, Jun. 1967, 8 pages.
Luo et al., "Simple Charts to Determine Hole Cleaning Requirements in Deviated Wells," IADC/SPE 27486, SPE/IADC Drilling Conference, Society of Petroleum Engineers, Feb. 15-18, 1994, 7 pages.
Paiaman et al., "Effect of Drilling Fluid Properties on Rate Penetration," Nafta vol. 60, No. 3, 2009, 6 pages.
Ranjbar, "Cutting Transport in Inclined and Horizontal Wellbore," University of Stavanger, Faculty of Science and Technology, Master's Thesis, Jul. 6, 2010, 137 pages.
Robinson and Morgan, "Effect of Hole Cleaning on Drilling Rate Performance," Paper Aade-04-Df-Ho-42, AADE 2004 Drilling Fluirds Conference, Houston, Texas, Apr. 6-7, 2004, 7 pages.
Robinson, "Economic Consequences of Poor Solids and Control," AADE 2006 Fluids Conference and Houston, Texas, Apr. 11-12, 2006, 9 pages.
Unegbu Celestine Tobenna, "Hole Cleaning Hydraulics," Universitetet o Stavanger, Faculty of Science and Technology, Master's Thesis, Jun. 15, 2010, 75 pages.
Xia et al., "A Cutting Concentration Model of a Vertical Wellbore Annulus in Deep-water Drilling Operation and its Application," Applied Mechanics and Materials, vol. 101-102, Sep. 27, 2011, 5 pages.
GCC Examination Report in GCC Appln. No. GC 2020-39806, dated Sep. 12, 2021, 4 pages.
Rubaii et al., "A new robust approach for hole cleaning to improve rate of penetration," presented at the SPE Kingdom of Saudi Arabia Annual Technical Symposium and Exhibition, Apr. 23-26, 2018, 40 pages.
PCT International Search Report and Written Opinion in International Appln. No. PCT/US2020/034218, dated Jul. 30, 2020, 15 pages.
Tejedor, "Real field deployment of smart fiber-optic surveillance system for pipeline integrity threat detection: Architectural issued and blind filed test results," Journal of Lightwave Technology, Feb. 2018, 36(4), 10 pages.
Baumgartner, "Maximizing the value of information from high-frequency downhole dynamics data," PhD. Thesis, The University of Texas, Austin, 2017, 237 pages.
EPO Communication Pursuant to Article 94(3) in European Appln No. 20732383.3, dated Nov. 17, 2022, 5 pages.

* cited by examiner

AUTOMATED DRILLING ADVISORY AND CONTROL SYSTEM

TECHNICAL FIELD

The present disclosure relates to oil field exploration.

BACKGROUND

In wellbore drilling, a drilling system causes a drill bit to rotate when in contact with a formation. The rotation of the drill bit breaks and fractures the formation to form the wellbore. The portions of the formation that are broken off during drilling are referred to as formation cuttings. In order to remove the cuttings from the wellbore, the drilling system circulates a drilling fluid (also referred to as drilling mud or mud) to the drill bit. The drilling fluid exits through drill bit nozzles to the bottom of the wellbore. The drilling fluid carries the formation cuttings from the wellbore to the surface. The ability of the drilling fluid to carry the formation cuttings out of the wellbore is referred to as a carrying capacity of the drilling fluid.

SUMMARY

The present disclosure describes an automated drilling advisory and control system (ACS). In an embodiment, while a drilling system is drilling a wellbore, the ACS monitors real-time values of a carrying capacity index (CCI) of a drilling fluid and a cutting concentration in an annulus (CCA) of the wellbore. If at least one of the values deviates from a respective range, then the ACS performs a corrective action to adjust the deviated value to be within its respective range. By maintaining the CCI and the CCA within the respective ranges, the ACS ensures that the drilling system performs a drilling operation efficiently.

Aspects of the subject matter described in this specification may be embodied in methods that include the actions of: obtaining, in real-time from one or more sensors of a drilling system, real-time drilling data of a drilling operation of drilling a wellbore; using the drilling data to calculate a carrying capacity index (CCI) of a drilling fluid and a cutting concentration in an annulus (CCA) of the wellbore; determining that at least one of the CCI and the CCA is outside a respective range; determining a corrective action to adjust the at least one of the CCI and the CCA to be within the respective range; and performing the corrective action.

The previously-described implementation is implementable using a computer-implemented method; a non-transitory, computer-readable medium storing computer-readable instructions to perform the computer-implemented method; and a computer system comprising a computer memory interoperably coupled with a hardware processor configured to perform the computer-implemented method/the instructions stored on the non-transitory, computer-readable medium. These and other embodiments may each optionally include one or more of the following features.

In a first aspect, performing the corrective action includes controlling the drilling system to adjust one or more drilling parameters that affect the at least one of the CCI and the CCA.

In a second aspect, performing the corrective action includes displaying, via a graphical user interface (GUI), drilling instructions to perform one or more actions to adjust the at least one of the CCI and the CCA.

In a third aspect, where the wellbore is vertical, and where the CCI is calculated using the equations:

$$CCI = \frac{\text{density} * K * V_{ann}}{(7.491)*(400000)}, K = \frac{510*\theta_{300}}{510^n}, \theta_{300} = PV + YP,$$

$$\theta_{600} = 2PV + YP, n = 3.32*\log\frac{\theta_{600}}{\theta_{300}}, \text{ and } V_{ann} = \frac{24.5*GPM}{HoleSize^2 - OD_{pipe}^2},$$

where HoleSize is a diameter of the wellbore, density is a density of the drilling fluid, K is a consistency index of the drilling fluid, $\theta_{300}$ is a drilling fluid viscosity reading at 300 revolutions per minute (RPM), $\theta_{600}$ is a drilling fluid viscosity reading at 600 RPM, PV is a plastic viscosity of the drilling fluid, YP is a yield point of the drilling fluid, $OD_{pipe}$ is a diameter of a drill pipe of the drilling system, and $V_{ann}$ is an annular velocity of the drilling fluid.

In a fourth aspect, where the wellbore is horizontal, and where the CCI is calculated using the equations:

$$CCI = \frac{K*TI}{3585*A_a*RF}, TI = GPM*\text{density}*\frac{RF}{834.5*7.481},$$

$$K = \frac{510*\theta_{300}}{510^n}, n = 3.32*\log\frac{\theta_{600}}{\theta_{300}}, RF = \frac{\left(\frac{PV}{YP}\right)+\left(\frac{YP}{PV}\right)}{2}, \text{ and}$$

$$A_a = \frac{\pi}{4*144}*[HoleSize^2 - OD_{pipe}^2],$$

where HoleSize is a diameter of the wellbore, GPM is a flow rate of the drilling fluid, density is a density of the drilling fluid, K is a consistency index of the drilling fluid, $\theta_{300}$ is a drilling fluid viscosity reading at 300 revolutions per minute (RPM), $\theta_{600}$ is a drilling fluid viscosity reading at 600 RPM, PV is a plastic viscosity of the drilling fluid, YP is a yield point of the drilling fluid, $OD_{pipe}$ is a diameter of a drill pipe of the drilling system, and $V_{ann}$ is an annular velocity of the drilling fluid, TI is a transport index of the drilling fluid, RF is a rheology factor, and $A_a$ is an annulus area.

In a fifth aspect, where the CCA is calculated using the equation $$CCA = \frac{ROP*(HoleSize)^2}{1471*GPM*TR},$$

where HoleSize is a diameter of the wellbore, ROP is a rate of penetration of a drilling tool of the drilling system, GPM is a flow rate of the drilling fluid, and TR is a transport ratio of the drilling fluid.

In a sixth aspect, where determining a corrective action to adjust the at least one of the CCI and the CCA to be within the respective range includes: determining that the CCI is greater than a first predetermined value; determining whether a ratio of a yield point (YP) of the drilling fluid to a plastic viscosity (PV) of the drilling fluid is greater than or equal to a second predetermined value; if the ratio is greater than or equal to the second predetermined value: determining that the corrective action is to increase the ratio to be greater than the second predetermined value; and if the ratio is less than the second predetermined value: determining that a flow rate of the drilling fluid is less than a predetermined optimum flow rate; and determining that the corrective action is to increase the flow rate of the drilling fluid to be greater than or equal to the predetermined optimum flow rate.

In a seventh aspect, where determining a corrective action to adjust the at least one of the CCI and the CCA to be within the respective range includes: determining that the CCI is less than a first predetermined value; determining that the CCA is less than or equal to a second predetermined value; determining whether a transport ratio (TR) of the drilling fluid is greater than or equal to a third predetermined value; and if the TR is less than the third predetermined value, determining that the corrective action is to increase the transport ratio to be greater than the third predetermined value.

In an eighth aspect, further including: if the TR is greater than or equal to the third predetermined value, determining whether a flow rate of the drilling fluid is greater than or equal to a predetermined optimum flow rate; and if the flow rate of the drilling fluid is less than the predetermined optimum flow rate, determining that the corrective action is to increase the flow rate of the drilling fluid to be greater than or equal to the predetermined optimum flow rate.

In a ninth aspect, further including: if the flow rate of the drilling fluid is greater than or equal to the predetermined optimum flow rate, determining whether the CCA is equal to the second predetermined value; and if the CCA is equal to the second predetermined value, determining that the corrective action is to increase a rate of penetration of a drilling tool of the drilling system.

The subject matter described in this specification can be implemented in particular implementations, so as to realize one or more of the following advantages. First, the technique of using both CCI and CCA to monitor and control a drilling operation is not used in commercial systems. Second, the disclosed system improves various aspects of drilling operations, such as hole cleaning and rate of penetration (ROP) of a drilling tool. These improvements help avoid stuck pipes, alleviate the equivalent circulating density (ECD) effect, reduce torque and drag, and improve transport cuttings in the annulus. Additionally, these improvements lead to cost effectiveness and contribute to well delivery. Third, the disclosed system can automatically monitor, measure, and direct users to adjust parameters associated with a drilling field to improve drilling operations.

DESCRIPTION OF DRAWINGS

Like reference numbers and designations in the various drawings indicate like elements.

DETAILED DESCRIPTION

Figure 1:
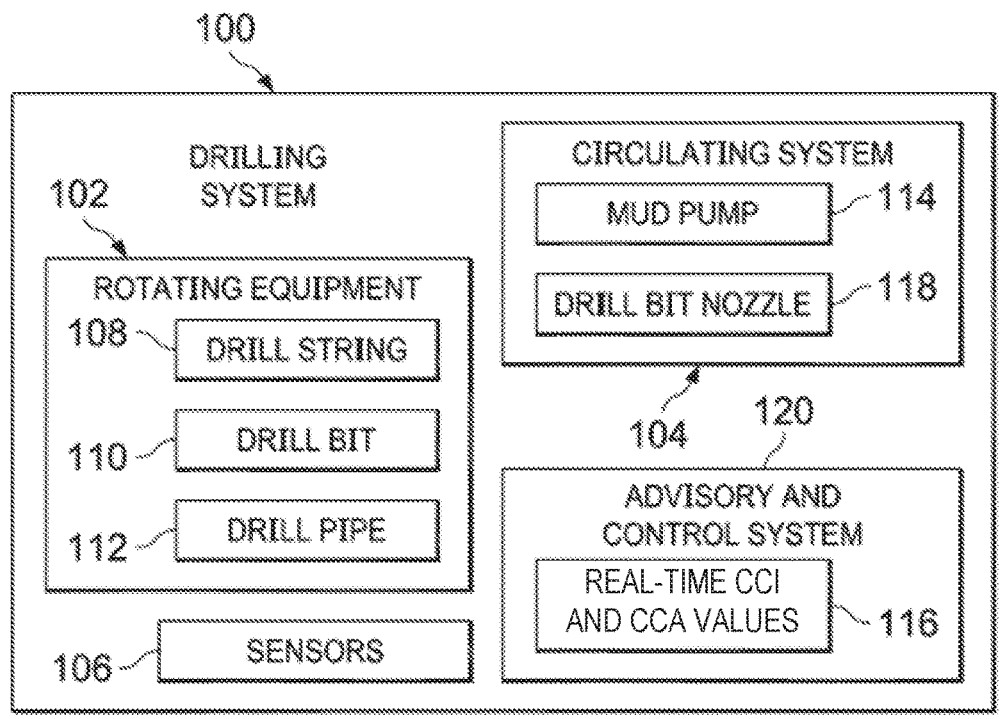
FIG. 1 is a block diagram of an example drilling system, according to some implementations of the present disclosure.

The following detailed description describes methods and systems for autonomously monitoring and controlling drilling operations. Various modifications, alterations, and permutations of the disclosed implementations can be made and will be readily apparent to those of ordinary skill in the art. Further, the general principles defined may be applied to other implementations and applications, without departing from the scope of the disclosure. In some instances, details unnecessary to obtain an understanding of the described subject matter may be omitted so as to not obscure one or more described implementations with unnecessary detail since such details are within the skill of one of ordinary skill in the art. The present disclosure is not intended to be limited to the described or illustrated implementations. Furthermore, the present disclosure is to be accorded the widest scope consistent with the described principles and features.

For the purposes of this disclosure, the terms "real-time," "real time," "realtime," or similar terms (as understood by one of ordinary skill in the art) mean that an action and a response are temporally proximate such that an individual perceives the action and the response occurring substantially simultaneously. For example, the time difference for a response to display (or for an initiation of a display) of data following the action of an individual to access the data may be less than 1 millisecond (ms), less than 1 second, or less than 5 seconds. While the requested data need not be displayed (or initiated for display) instantaneously, it is displayed (or initiated for display) without any intentional delay, taking into account processing limitations of a described computing system and time required to, for example, gather, accurately measure, analyze, process, store, and/or transmit the data.

Many dynamic factors affect drilling operations that are performed by drilling systems. For example, dynamic factors, such as wellbore angle, cuttings type, and cuttings size, affect a carrying capacity of a drilling fluid. Drilling models and simulations attempt to predict values of the dynamic factors to account for the factors when drilling the wellbore. However, in practice, models and simulations do not account for the real-time values of the dynamic factors. As a result, drilling operations that rely on these models and simulations are often inefficient.

Disclosed is a drilling advisory and control system (ACS) that monitors and controls a drilling operation based on real-time values of drilling parameters. In an implementation, the ACS uses real-time values of a carrying capacity index of a drilling fluid (CCI) and a cutting concentration in an annulus (CCA) to monitor and control a drilling operation. The CCI and the CCA can be used to derive many drilling parameters. Thus, by monitoring the real-time CCI and CCA values, the ACS can determine a status of several aspects of the drilling operation. Furthermore, experimentation has shown that maintaining CCI and CCA values within respective ranges ensures an efficient drilling operation. Therefore, while monitoring the real-time CCI and CCA values, the ACS can detect that at least one of the values has deviated from its respective range of values. In response, the ACS performs a corrective action to adjust the deviated value to be within the respective range.

FIG. 1 is a block diagram of an example drilling system 100, according to some implementations. The drilling system 100 includes rotating equipment 102, circulating system 104, sensors 106, and drilling advisory and control system (ACS) 120. The rotating equipment 102, which is responsible for rotary drilling, includes, among other tools not illustrated, drill string 108, drill bit 110, and drill pipe 112. The circulating system 104, which is responsible for the circulation of drilling fluid, includes, among other tools not illustrated, mud pump 114 and drill bit nozzle 118. The sensors 106 include sensors, tools, and devices that are configured for real-time surface and down-wellbore measurements. The surface measurements include rate of penetration (ROP), rotary torque, mudflow volume, mud pressure, mud resistivity, and gas readings. The down-wellbore measurements include measurement-while-drilling (MWD) and logging-while-drilling (LWD). The ACS 120 is a computer-based system that is configured to monitor drilling operations, provide drilling recommendations to operators, and control the drilling system 100.

To drill a wellbore, the drilling system 100 lowers the drill bit 110, which is attached to the drill string 108, into a well until the drill bit 110 makes contact with a formation. Once in contact, the drill bit 110 is rotated to break and fracture the formation, thereby forming the wellbore. As the rotating equipment 102 drills the wellbore, the mud pump 114 withdraws drilling fluid from a mud pit and pumps the drilling fluid down the drill string 108 through the drill bit nozzles 118 that are located on the drill bit 110. The drilling fluid flows to the bottom of the wellbore and upward to the surface via an annulus formed between the drilling string 108 and the walls of the wellbore. When flowing to the surface, the drilling fluid carries portions of the formation, called cuttings, that are fractured by the rotating drill bit 110. At the surface, the circulating system 104 filters the cuttings from the drilling fluid and pumps the drilling fluid back down to the bottom the wellbore.

In an embodiment, the ACS 120 is configured to monitor the drilling operation, provide drilling recommendations to operators of the drilling system 100, and control the drilling system 100. In an implementation, the ACS 120 calculates and monitors real-time CCA and CCI values 116. The ACS 120 uses the real-time CCA and CCI values 116 to determine a status of the drilling operation. In particular, the ACS 120 determines based on the real-time CCA and CCI values whether the drilling operation is being performed efficiently. If ACS 120 determines that an improvement can be made to the drilling operation, then the ACS 120 performs a corrective action.

In an implementation, calculations of real-time CCA and CCI values 116 use real-time drilling data, such as flow rate, ROP, and mud properties. In an example, CCA is calculated using equation (1):

$$CCA = \frac{ROP*(HoleSize)^2}{1471*GPM*TR}. \quad (1)$$

In equation (1), HoleSize is the diameter of the wellbore (in feet), ROP is the rate of penetration of the drill bit 110 (in feet/hour), GPM is the flow rate of the drilling fluid (in gallons/minutes), and TR is transport ratio of the drilling fluid. In one example, TR is assigned a constant value of 0.55.

The equations for calculating real-time CCI values is different for horizontal wells and vertical wells. In an example, CCI for a vertical well is calculated using equations (2)-(7):

$$CCI = \frac{density*K*V_{ann}}{(7.491)*(400000)} \quad (2)$$

$$K = \frac{510*\theta_{300}}{510^n} \quad (3)$$

$$\theta_{300} = PV + YP \quad (4)$$

$$\theta_{600} = 2PV + YP \quad (5)$$

$$n = 3.32*\log\frac{\theta_{600}}{\theta_{300}} \quad (6)$$

$$V_{ann} = \frac{24.5*GPM}{HoleSize^2 - OD_{pipe}^2} \quad (7)$$

In these equations, density is the drilling fluid density (in pounds per cubic foot), K is a consistency index of the drilling fluid (in poise), $\theta_{300}$ is a drilling fluid viscosity reading (using a viscometer) at 300 revolutions per minute (RPM), $\theta_{600}$ is a drilling fluid viscosity reading (using a viscometer) at 600 RPM, PV is a plastic viscosity of the drilling fluid (in poise), YP is a yield point (in pound/100 square feet) of the drilling fluid, ODpipe is a diameter of the drill pipe (in feet), and $V_{ann}$ is an annular velocity of the drilling fluid (in feet/minute).

In an example, CCI for a horizontal well is calculated using equations (8)-(11):

$$CCI = \frac{K*TI}{3585*A_a*RF} \quad (8)$$

$$TI = GPM*density*\frac{RF}{834.5*7.481} \quad (9)$$

$$RF = \frac{\left(\frac{PV}{YP}\right)+\left(\frac{YP}{PV}\right)}{2} \quad (10)$$

$$A_a = \frac{\pi}{4*144}*[HoleSize^2 - OD_{pipe}^2] \quad (11)$$

In these equations, TI is a transport index of the drilling fluid, RF is a rheology factor, and $A_a$ is an annulus area (in square feet).

Figure 2:
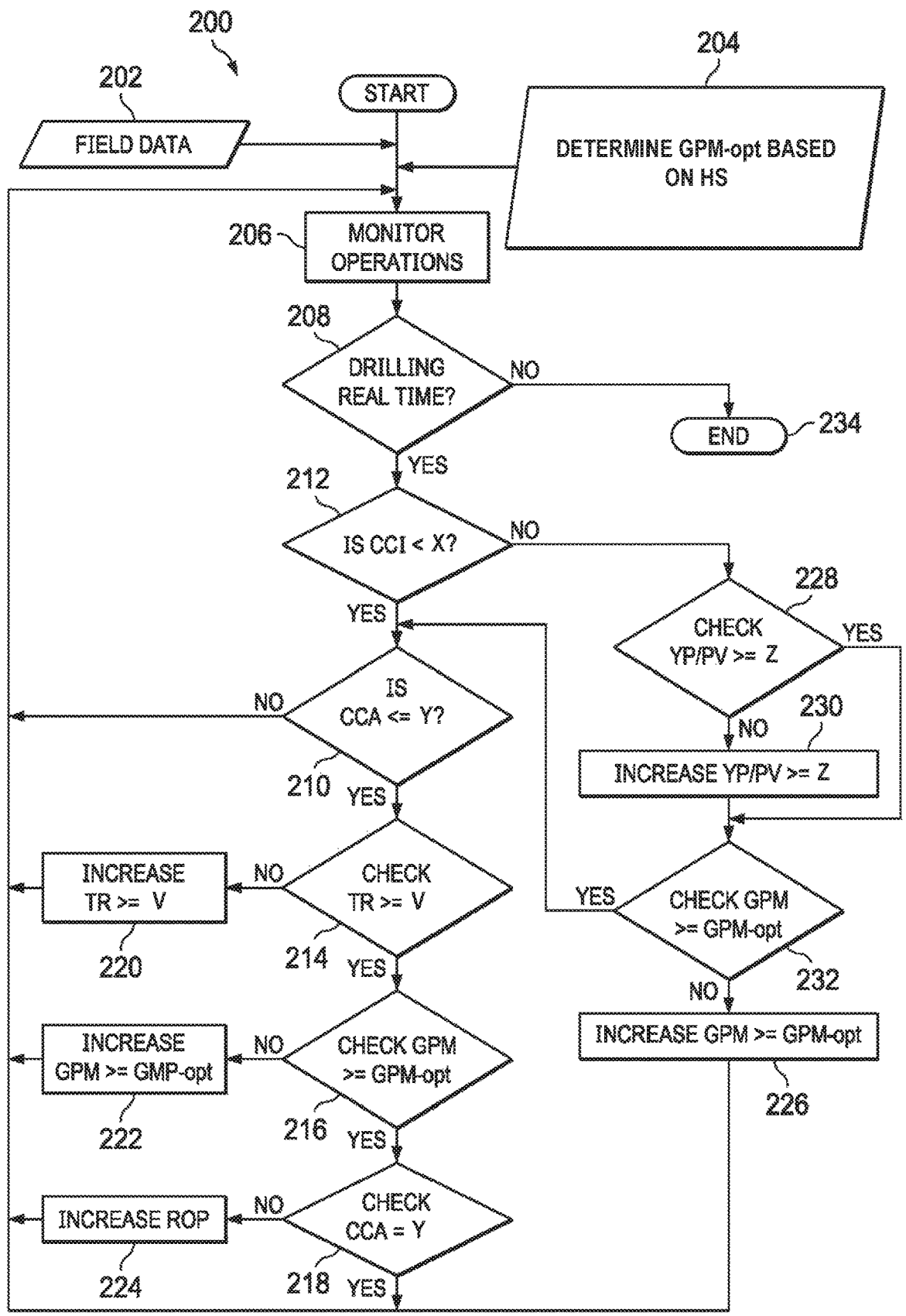
FIG. 2 is a flowchart of an example process for autonomously monitoring a drilling operation, according to some implementations of the present disclosure.
Figure 3A:
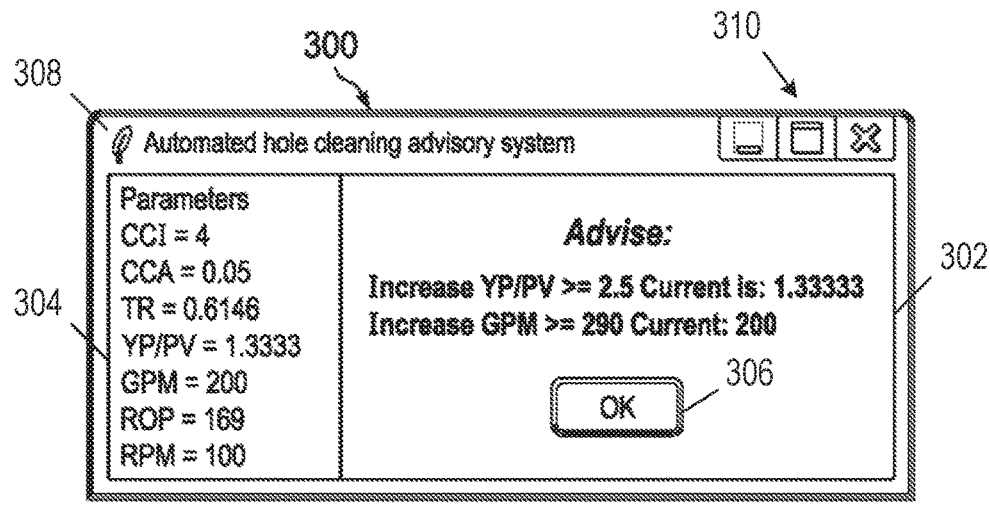
FIGS. 3A, 3B, 3C, 3D, and 3E are example graphical user interfaces (GUIs) that provide drilling recommendations, according to some implementations of the present disclosure.
Figure 3B:
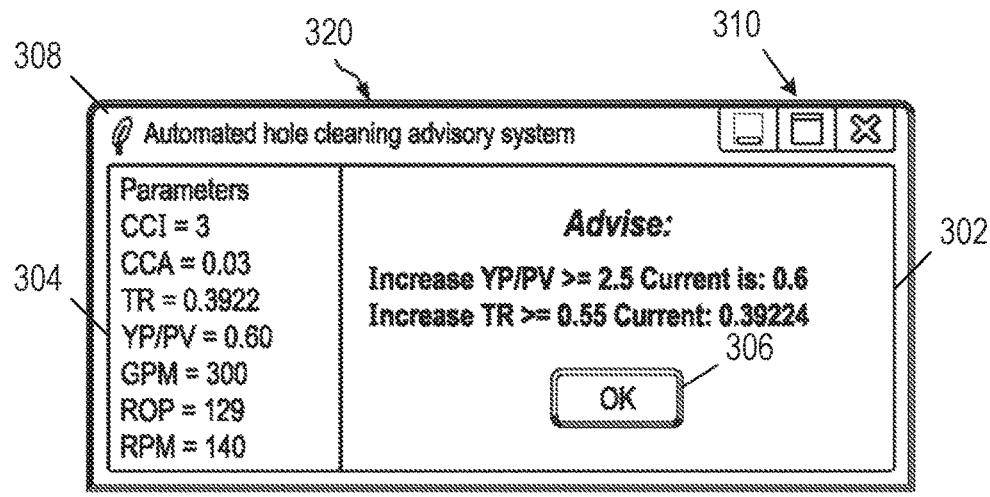
Figure 3C:
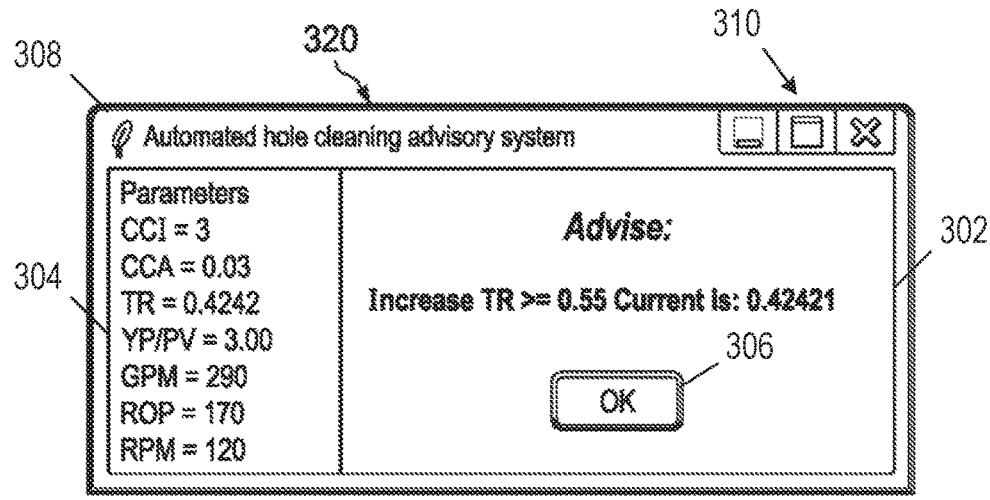
Figure 3D:
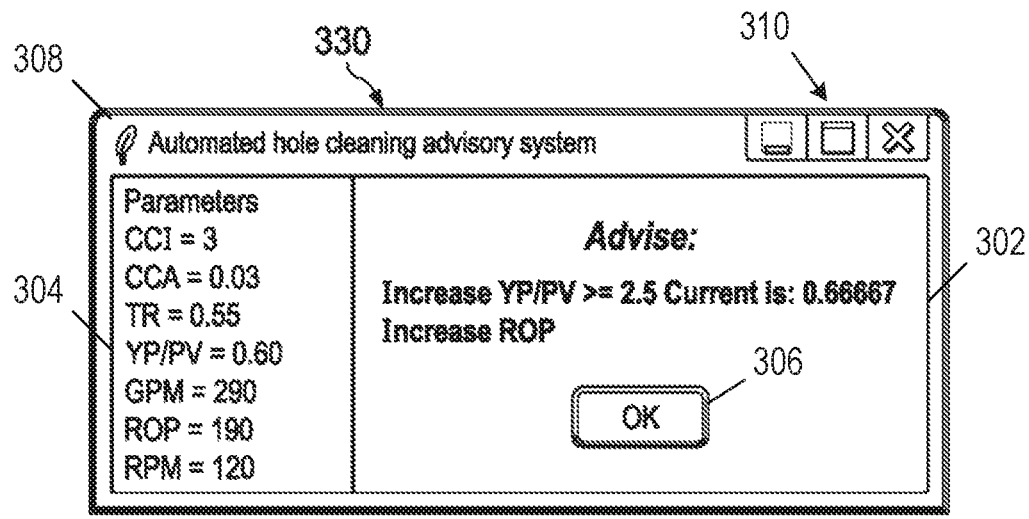
Figure 3E:
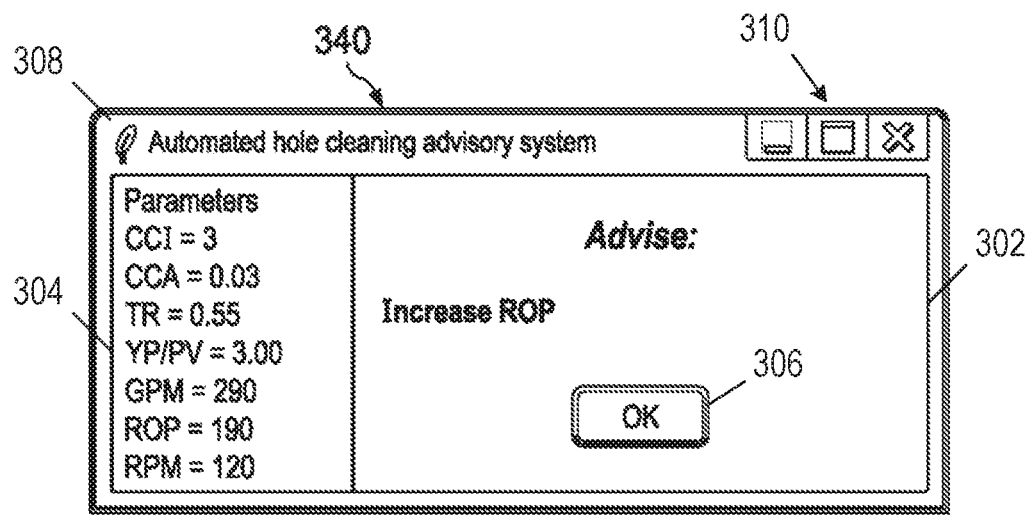

FIG. 2 is a flowchart of an example process 200 for autonomously monitoring a drilling operation, according to some implementations. In an embodiment, the ACS 120 executes the process 200 to autonomously monitor and control the drilling operation.

The process 200 starts at step 202, which involves the ACS 120 receiving drilling operation data (also referred to as "field data"). The drilling operation data includes a hole size of the wellbore, dimensions of the drill pipe, and mud properties (for example, PV, YP, and density). Additionally, the drilling operation data includes mechanical parameters, such as GPM, ROP, torque (that is, the movement required to rotate the drilling pipe), spindle speed (that is, the rotation frequency of the spindle of the drilling system, measured in RPM), weight on bit (that is, the amount of downward force exerted on the drilling bit provided by the thick-walled tubular pieces in the drilling assembly), and standard pipe pressure (that is the summation of pressure loss in annulus, pressure loss in drill string, pressure loss in bottom hole assembly (BHA) and pressure loss across the bit).

At step 204, the ACS 120 determines an optimum value (GPM-opt) for the mud flow rate (GPM) based on the hole size (HS) of the wellbore. In particular, the ACS 120 may use a look up table to determine a GPM-opt that corresponds to the HS of the wellbore. In an implementation, the table is populated by experimentally determining a respective optimum mud flow rate for different hole sizes. In particular, the respective optimum mud flow rates are determined based on experiments done in different drilling fields and under different conditions. For example, experimentation on a hole size of 16 inches in different hole-sections (vertical, deviated, and horizontal) shows that the optimum value for the mud flow rate is 1000 GPM. As another example, experimentation shows that for a hole size of 22 inches, the optimum value for the mud flow rate is 1100 GPM. Other hole sizes and corresponding optimum mud flow rates are possible.

At step 206, the ACS 120 begins monitoring the drilling operation. While at step 206, the ACS 120 periodically moves to step 208 to determine whether the drilling system is actively drilling the wellbore. At step 208, if the drilling system is not actively drilling, then the ACS 120 moves to step 234 of ending the process 200. Alternatively, if the drilling system is actively drilling the wellbore, then the ACS 120 moves to step 212.

At step 212, the ACS 120 determines whether the real-time value of CCI is less than a constant, X, that serves as an upper bound on a range of acceptable values for CCI. Accordingly, the range of acceptable values for CCI is less than X. As described below, X is an experimentally derived value. To compare the real-time value of CCI to X, the ACS 120 determines the real-time value of CCI using equations (2)-(7) for vertical wells and equations (8)-(11) for horizontal wells. The ACS 120 then compares the real-time CCI value to X. If the real-time CCI value is less than X (that is, the CCI value is within the acceptable range), then the ACS 120 moves to step 210.

At step 210, the ACS 120 determines whether the real-time value of CCA is less than or equal to a constant, Y, that serves as a lower bound on a range of acceptable values for CCA. Accordingly, the range of acceptable values for CCA is greater than Y. As described below, Y is an experimentally derived value. To compare the real-time value of CCA to Y, the ACS 120 determines the real-time value of CCA using equation (1). The ACS 120 then compares the real-time CCA value to Y. If the real-time value is not less than or equal to Y (that is, the CCA value is within the acceptable range), then the ACS 120 returns to step 206 of monitoring the drilling operation because both CCI and CCA are within their respective ranges.

Conversely, if at step 210 the real-time value of CCA is less than or equal to Y (that is, the CCA value is not within the acceptable range), then the ACS 120 performs one or more tests (in steps 214, 216, and 218) to determine if a drilling parameter needs to adjusted in a corrective action.

In a first test at step 214, the ACS 120 determines whether TR is greater than or equal to a constant, V. As described below, V is an experimentally derived value. If the value of TR is not greater than or equal to V, then the ACS 120 moves to step 220. At step 220, the ACS 120 determines to increase TR to be greater than or equal to V. In an implementation, the TR is calculated using equation (12):

$$TR = \left(1 - \frac{V_s}{V_{ann}}\right) \quad (12)$$

In equation (12), $V_s$ is a cuttings slip velocity (in feet/min) and $V_{ann}$ is an annular velocity (in feet/min) that is calculated using equation (7). In response to determining moving to step 220, the ACS 120 performs a corrective action to increase the TR. In one implementation, the ACS 120 outputs, via a graphical user interface (GUI), instructions, perhaps to an operator, to suggest to increase TR. In another implementation, the ACS 120 controls the drilling system 100 to increase TR autonomously. In particular, the ACS 120 autonomously adjusts one or more drilling parameters (for example, $V_{ann}$) to increase TR. In an example, autonomously increasing TR involves increasing TR to be equal to V. In another example, autonomously increasing TR involves increasing TR to be equal to predetermined threshold value above V.

Conversely, if at step 214 the ACS 120 determines that the value of TR is greater than or equal to V, then the ACS 120 moves to step 216. At step 216, the ACS 120 determines whether the flow rate is greater than or equal to the optimum flow rate (set at step 204). In an implementation, the flow rate is determined from the field data received in step 202. If the flow rate is not greater than or equal to the optimum flow rate, the ACS 120 moves to step 222, where the ACS 120 determines to increase the flow to be greater than or equal to the optimum flow rate. The ACS 120 then performs a corrective action to increase the flow rate. In one implementation, the ACS 120 outputs, via the GUI, instructions that suggests to an operator to increase the flow rate. In another implementation, the ACS 120 controls the drilling system 100 to increase the flow rate autonomously. In particular, the ACS 120 autonomously controls drilling equipment (for example, the mud pump 114) to increase flow rate. In an example, autonomously increasing the flow rate involves increasing flow rate to be equal to GPM-opt. In another example, autonomously increasing the flow rate involves increasing the flow rate to be equal to predetermined threshold value above GPM-opt.

However, if at step 216 the ACS 120 determines that the value of the flow rate is greater than or equal to the optimum flow rate, then the ACS 120 moves to step 218 where the ACS 120 determines, using equation (1), whether the CCA is equal to Y. If the value of CCA is not equal to Y, the ACS 120 moves to step 224, where the ACS 120 determines to increase the ROP. In response, the ACS 120 performs a corrective action to increase the ROP. In one implementation, the ACS 120 outputs, via the GUI, instructions to increase the ROP. In another implementation, the ACS 120 controls the drilling system 100 to increase the ROP autonomously by controlling drilling equipment to increase the ROP. In particular, equation (1) can be used to solve for a new ROP based on a desired value of CCA. In one example, the desired value of CCA is Y. In another example, the desired value of CCA is a predetermined threshold value more than Y.

If at step 218 the value of the CCA is equal to Y, then the ACS 120 moves back to step 206 of monitoring the drilling operations.

Returning to step 212, if the value of the CCI is not less than X (that is, not within the acceptable range), then the ACS 120 performs one or more tests (in steps 228 and 232) to determine if a drilling parameter needs to adjusted in a corrective action.

At step 228, the ACS 120 determines whether the ratio of YP to PV is greater than or equal to a constant, Z. As described previously, the values of YP and PV can be determined using a viscometer, and as described below, Z is an experimentally derived value. If the ratio is not greater than or equal to Z, then the ACS 120 moves to step 230, where the ACS 120 determines to increase the ratio of YP to PV to be greater than or equal to Z. The ACS 120 then performs a corrective action to increase the ratio. In one implementation, the ACS 120 outputs, via the GUI, instructions to suggest to an operator to increase the ratio. In another implementation, the ACS 120 controls the drilling system 100 to increase the ratio autonomously by adjusting PV, YP, or both. In particular, to lower PV, the drilling fluid is diluted, perhaps by increasing the drilling fluid flow rate, to reduce the solids content. YP is lowered by adding thinning agent and is increased by adding flocculant (for example, lime). In an example, the ACS 120 adjusts the ratio, perhaps by trial and error, until the ratio is equal to Z. In another example, the ACS 120 adjusts the ratio, perhaps by trial and error, until the ratio is equal to a predetermined threshold value above Z. Then the process proceeds to step 232.

Conversely, if at step 228 the ratio is greater than or equal to Z, then the ACS 120 moves to step 232 of determining whether the flow rate is greater than or equal to the optimum flow rate (set in step 204). If the flow rate is greater than or equal to the optimum flow rate, then the ACS 120 moves to step 210 of determining whether the CCA is less than or equal to Y. Conversely, if the flow rate is not greater than or equal to the optimum flow rate, then the ACS 120 moves to step 226, where the ACS 120 determines to increase the flow rate to be greater than or equal to the optimum flow rate. The ACS 120 then performs a corrective action in order to increase the flow rate. In one implementation, the ACS 120 outputs, via the GUI, instructions to an operator to suggest increasing the flow rate. In another implementation, the ACS 120 controls the drilling system 100 to increase the GPM autonomously. In particular, the ACS 120 autonomously controls drilling equipment (for example, the mud pump 114) to increase flow rate. In an example, autonomously increasing the flow rate involves increasing flow rate to be equal to GPM-opt. In another example, autonomously increasing the flow rate involves increasing the flow rate to be equal to predetermined threshold value above GPM-opt. The ACS 120 then moves back to step 206 of monitoring the drilling operation.

The corrective actions performed by the ACS 120 improve drilling operations by maintaining the CCA and the CCI within their respective ranges. In an embodiment, the acceptable ranges for different parameters (such as CCI, CCA, TR, YP/PV) used in the process 200 are determined so as to optimize drilling operations. In particular, the ranges are determined based on experiments done in different drilling fields and under different conditions. For example, after finishing a study on a 16" hole-section and performed implementation of the model in fields for different hole-sections (vertical, deviated, and horizontal), the desired threshold value for CCI is determined as less than X in a 16" hole-section. This means that if the annulus of a drilled hole-section is less than the annulus of the hole-section of the 16" hole section, a CCI value that is less than X can ensure the optimum hole cleaning in various hole-sections for different sizes and types. Similarly, a determination that the threshold value of CCA is at least equal to Y is made based on experience and literature. It is also noticed that when CCA has a value of at least Y that the system has the smoothness with generated cuttings while drilling. In this way, maintaining CCI less than X while simultaneously maintaining the value of CCA to be at least Y ensures an efficient cleaning of generated cuttings. Likewise, the threshold value of YP/PV is a dominant factor of the rheology of drilling fluid that can control the consistency index and shear thinning. Applying a value of YP/PV equal to or greater than Z can ensure the CCI is less than X. In an example, based on experimentation, X is determined to be 5, Y is determined to be 0.05, V is determined to be 0.55, and Z is determined to be 2.5. Other examples are also possible. For instance, Y is determined to be 0.06-0.08 if the solid removal equipment of a mud system is efficient enough.

FIGS. 3A, 3B, 3C, 3D, and 3E are example graphical user interfaces (GUIs) 300, 312, 320, 330, and 340 that provide drilling recommendations, according to some implementations. As shown in figures, each GUI includes a section 304 that displays real-time values of drilling parameters, such as CCI, CCA, TR, YP/PV, GPM, ROP, and RPM. Then, in section 302, the each GUI displays a recommendation from the ACS 120 that provides instructions to perform certain rectifying actions. Each GUI also has an acknowledgement button 306 to ensure that the instruction provided by the system is received. Additionally, each GUI includes a header section 308 and control icons 310.

Figure 4:
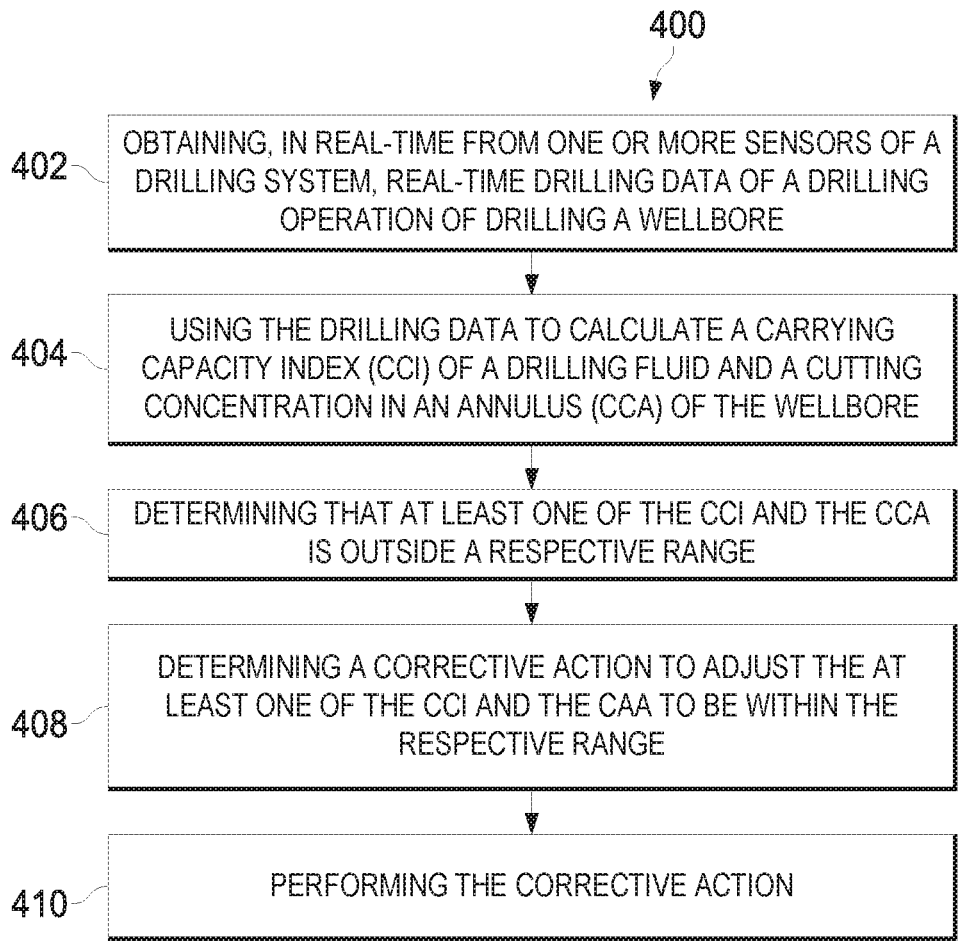
FIG. 4 is a flowchart of an example method for autonomously monitoring a drilling operation, according to some implementations of the present disclosure.

FIG. 4 is a flowchart of an example method for autonomously advising and controlling a drilling operation, according to some implementations of the present disclosure. For clarity of presentation, the description that follows generally describes method 400 in the context of the other figures in this description. However, it will be understood that method 400 can be performed, for example, by any suitable system, environment, software, and hardware, or a combination of systems, environments, software, and hardware, as appropriate. In some implementations, various steps of method 400 can be run in parallel, in combination, in loops, or in any order.

The method 400 begins at step 402, which involve obtaining, in real-time from one or more sensors of a drilling system, real-time drilling data of a drilling operation of drilling a wellbore.

At step 404, the method 400 involves using the drilling data to calculate a carrying capacity index (CCI) of a drilling fluid and a cutting concentration in an annulus (CCA) of the wellbore.

At step 406, the method 400 involves determining that at least one of the CCI and the CCA is outside a respective range.

At step 408, the method 400 involves determining a corrective action to adjust the at least one of the CCI and the CCA to be within the respective range.

At step 410, the method 400 involves performing the corrective action.

Figure 5:
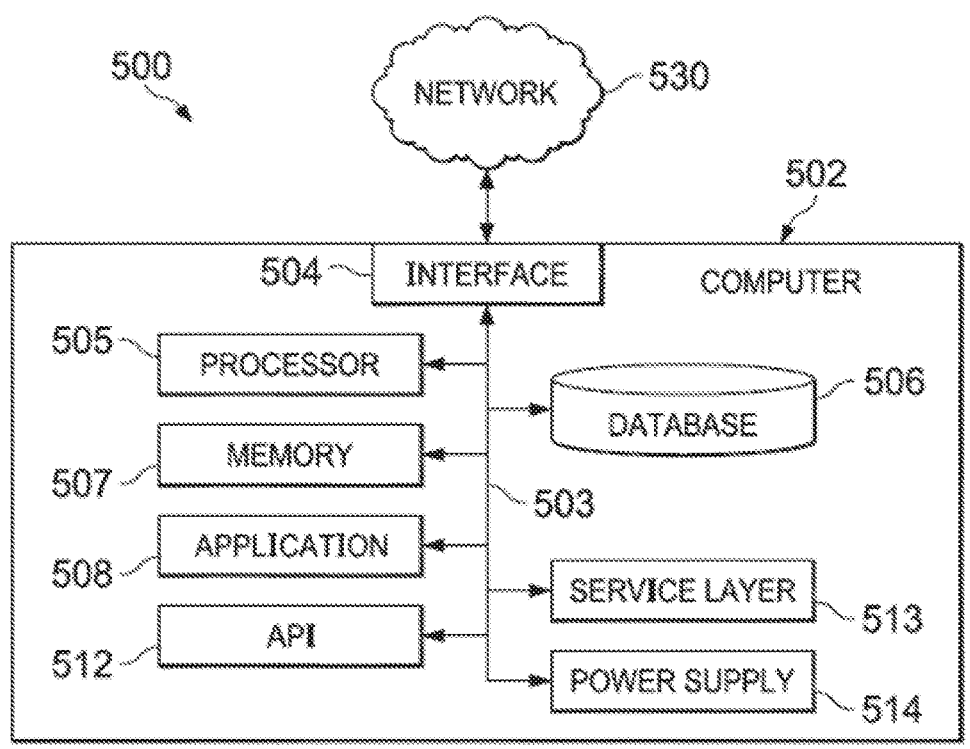
FIG. 5 is a block diagram illustrating an example computer system used to provide computational functionalities associated with described algorithms, methods, functions, processes, flows, and procedures as described in the present disclosure, according to some implementations of the present disclosure.

FIG. 5 is a block diagram of an example computer system 500 used to provide computational functionalities associated with described algorithms, methods, functions, processes, flows, and procedures described in the present disclosure, according to some implementations of the present disclosure. The illustrated computer 502 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 502 can include input devices such as keypads, keyboards, and touch screens that can accept user information. Also, the computer 502 can include output devices that can convey information associated with the operation of the computer 502. The information can include digital data, visual data, audio information, or a combination of information. The information can be presented in a graphical user interface (UI) (or GUI).

The computer 502 can serve in a role as a client, a network component, a server, a database, a persistency, or components of a computer system for performing the subject matter described in the present disclosure. The illustrated computer 502 is communicably coupled with a network 530. In some implementations, one or more components of the computer 502 can be configured to operate within different environments, including cloud-computing-based environments, local environments, global environments, and combinations of environments.

Generally, the computer 502 is an electronic computing device operable to receive, transmit, process, store, and manage data and information associated with the described subject matter. According to some implementations, the computer 502 can also include, or be communicably coupled with, an application server, an email server, a web server, a caching server, a streaming data server, or a combination of servers.

The computer 502 can receive requests over network 530 from a client application (for example, executing on another computer 502). The computer 502 can respond to the received requests by processing the received requests using software applications. Requests can also be sent to the computer 502 from internal users (for example, from a command console), external (or third) parties, automated applications, entities, individuals, systems, and computers.

Each of the components of the computer 502 can communicate using a system bus 503. In some implementations, any or all of the components of the computer 502, including hardware or software components, can interface with each other or the interface 504 (or a combination of both), over the system bus 503. Interfaces can use an application programming interface (API) 512, a service layer 513, or a combination of the API 512 and service layer 513. The API 512 can include specifications for routines, data structures, and object classes. The API 512 can be either computer-language independent or dependent. The API 512 can refer to a complete interface, a single function, or a set of APIs.

The service layer 513 can provide software services to the computer 502 and other components (whether illustrated or not) that are communicably coupled to the computer 502. The functionality of the computer 502 can be accessible for all service consumers using this service layer. Software services, such as those provided by the service layer 513, can provide reusable, defined functionalities through a defined interface. For example, the interface can be software written in JAVA, C++, or a language providing data in extensible markup language (XML) format. While illustrated as an integrated component of the computer 502, in alternative implementations, the API 512 or the service layer 513 can be stand-alone components in relation to other components of the computer 502 and other components communicably coupled to the computer 502. Moreover, any or all parts of the API 512 or the service layer 513 can be implemented as child or sub-modules of another software module, enterprise application, or hardware module without departing from the scope of the present disclosure.

The computer 502 includes an interface 504. Although illustrated as a single interface 504 in FIG. 5, two or more interfaces 504 can be used according to particular needs, desires, or particular implementations of the computer 502 and the described functionality. The interface 504 can be used by the computer 502 for communicating with other systems that are connected to the network 530 (whether illustrated or not) in a distributed environment. Generally, the interface 504 can include, or be implemented using, logic encoded in software or hardware (or a combination of software and hardware) operable to communicate with the network 530. More specifically, the interface 504 can include software supporting one or more communication protocols associated with communications. As such, the network 530 or the interface's hardware can be operable to communicate physical signals within and outside of the illustrated computer 502.

The computer 502 includes a processor 505. Although illustrated as a single processor 505 in FIG. 5, two or more processors 505 can be used according to particular needs, desires, or particular implementations of the computer 502 and the described functionality. Generally, the processor 505 can execute instructions and can manipulate data to perform the operations of the computer 502, including operations using algorithms, methods, functions, processes, flows, and procedures as described in the present disclosure.

The computer 502 also includes a database 506 that can hold data for the computer 502 and other components connected to the network 530 (whether illustrated or not). For example, database 506 can be an in-memory, conventional, or a database storing data consistent with the present disclosure. In some implementations, database 506 can be a combination of two or more different database types (for example, hybrid in-memory and conventional databases) according to particular needs, desires, or particular implementations of the computer 502 and the described functionality. Although illustrated as a single database 506 in FIG. 5, two or more databases (of the same, different, or combination of types) can be used according to particular needs, desires, or particular implementations of the computer 502 and the described functionality. While database 506 is illustrated as an internal component of the computer 502, in alternative implementations, database 506 can be external to the computer 502.

The computer 502 also includes a memory 507 that can hold data for the computer 502 or a combination of components connected to the network 530 (whether illustrated or not). Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 5, two or more memories 507 (of the same, different, or combination of types) can be used according to particular needs, desires, or particular implementations of the computer 502 and the described functionality. While memory 507 is illustrated as an internal component of the computer 502, in alternative implementations, memory 507 can be external to the computer 502.

The application 508 can be an algorithmic software engine providing functionality according to particular needs, desires, or particular implementations of the computer 502 and the described functionality. For example, application 508 can serve as one or more components, modules, or applications. Further, although illustrated as a single application 508, the application 508 can be implemented as multiple applications 508 on the computer 502. In addition, although illustrated as internal to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion and management circuits, including recharging, standby, and power management functionalities. In some implementations, the power-supply 514 can include a power plug to allow the computer 502 to be plugged into a wall socket or a power source to, for example, power the computer 502 or recharge a rechargeable battery.

There can be any number of computers 502 associated with, or external to, a computer system containing computer 502, with each computer 502 communicating over network 530. Further, the terms "client," "user," and other appropriate terminology can be used interchangeably, as appropriate, without departing from the scope of the present disclosure. Moreover, the present disclosure contemplates that many users can use one computer 502 and one user can use multiple computers 502.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method, comprising:
obtaining, in real-time from one or more sensors of a drilling system, real-time drilling data of a drilling operation of drilling a wellbore;
using the real-time drilling data to calculate a carrying capacity index (CCI) of a drilling fluid and a cutting concentration in an annulus (CCA) of the wellbore;
determining that at least one of the CCI and the CCA is outside a respective range;
determining a corrective action to adjust the at least one of the CCI and the CCA to be within the respective range, wherein determining the corrective action comprises:
  (i) determining that the CCI is less than a first predetermined value, wherein the first predetermined value is an upper bound of the respective range of values for the CCI,
  (ii) determining that the CCA is less than or equal to a second predetermined value, wherein the second predetermined value is a lower bound of the respective range of values for the CCA,
  (iii) determining whether a transport ratio, TR, of the drilling fluid is greater than or equal to a third predetermined value,
  (iv) if the TR is less than the third predetermined value, determining that the corrective action is to increase the transport ratio to be greater than the third predetermined value, and
  (iv) if the TR is greater than or equal to the third predetermined value, determining whether a flow rate of the drilling fluid is greater than or equal to a predetermined optimum flow rate, and
  if the flow rate of the drilling fluid is less than the predetermined optimum flow rate, determining that the corrective action is to increase the flow rate of the drilling fluid to be greater than or equal to the predetermined optimum flow rate; and
performing the corrective action, wherein performing the corrective action comprises controlling the drilling system to adjust one or more drilling parameters that affect the at least one of the CCI and the CCA.

2. The computer-implemented method of claim 1, wherein performing the corrective action comprises:
displaying, via a graphical user interface (GUI), drilling instructions to perform one or more actions to adjust the at least one of the CCI and the CCA.

3. The computer-implemented method of claim 1, wherein the wellbore is vertical, and wherein the CCI is calculated using equations comprising:

$$CCI = \frac{\text{density} * K * V_{ann}}{(7.491) * (400000)},$$

$$K = \frac{510 * \theta_{300}}{510^n},$$

$$\theta_{300} = PV + YP,$$

$$\theta_{600} = 2PV + YP,$$

$$n = 3.32 * \log\frac{\theta_{600}}{\theta_{300}}, \text{ and}$$

$$V_{ann} = \frac{24.5 * GPM}{\text{HoleSize}^2 - OD_{pipe}^2},$$

wherein HoleSize is a diameter of the wellbore in units of feet (ft),
GPM is the flow rate of the drilling fluid in units of gallons/minute,
density is a density of the drilling fluid in units of pounds per cubic feet (lb/ft$^3$),
K is a consistency index of the drilling fluid in units of poise,
$\theta_{300}$ is a drilling fluid viscosity reading at 300 revolutions per minute (RPM),
$\theta_{600}$ is a drilling fluid viscosity reading at 600 RPM,
PV is a plastic viscosity of the drilling fluid in units of poise,
YP is a yield point of the drilling fluid in units of lb/100 ft$^2$,
$OD_{pipe}$ is a diameter of a drill pipe of the drilling system in units of ft, and
$V_{ann}$ is an annular velocity of the drilling fluid in units of ft/minute.

4. The computer-implemented method of claim 1, wherein the wellbore is horizontal, and wherein the CCI is calculated using equations comprising:

$$CCI = \frac{K * TI}{3585 * A_a * RF},$$

$$TI = GPM * \text{density} * \frac{RF}{834.5 * 7.481},$$

$$K = \frac{510 * \theta_{300}}{510^n},$$

$$n = 3.32 * \log\frac{\theta_{600}}{\theta_{300}},$$

$$RF = \frac{\left(\frac{PV}{YP}\right) + \left(\frac{YP}{PV}\right)}{2}, \text{ and}$$

$$A_a = \frac{\pi}{4 * 144} * [\text{HoleSize}^2 - OD_{pipe}^2],$$

wherein HoleSize is a diameter of the wellbore in units of feet (ft), GPM is the flow rate of the drilling fluid in units of gallons/minute, density is a density of the drilling fluid in units of pounds per cubic feet (lb/ft$^3$), K is a consistency index of the drilling fluid in units of poise, $\theta_{300}$ is a drilling fluid viscosity reading at 300 revolutions per minute (RPM), $\theta_{600}$ is a drilling fluid viscosity reading at 600 RPM, PV is a plastic viscosity of the drilling fluid in units of poise, YP is a yield point of the drilling fluid in units of lb/100 ft$^2$, $OD_{pipe}$ is a diameter of a drill pipe of the drilling system in units of ft, and $V_{ann}$ is an annular velocity of the drilling fluid in units of ft/minute, TI is a transport index of the drilling fluid, RF is a rheology factor, and $A_a$ is an annulus area in units of ft$^2$.

5. The computer-implemented method of claim 1, wherein the CCA is calculated using an equation:

$$CCA = \frac{ROP * (\text{HoleSize})^2}{1471 * GPM * TR},$$

wherein HoleSize is a diameter of the wellbore in units of feet (ft), ROP is a rate of penetration of a drilling tool of the drilling system in units of ft/hour, GPM is the flow rate of the drilling fluid in units of gallons/minute, and TR is the transport ratio of the drilling fluid.

6. The computer-implemented method of claim 1, wherein determining the corrective action to adjust the at least one of the CCI and the CCA to be within the respective range comprises:
  determining that the CCI is greater than the first predetermined value;
  determining whether a ratio of a yield point (YP) of the drilling fluid to a plastic viscosity (PV) of the drilling fluid is greater than or equal to a fourth predetermined value;
  if the ratio is less than to the fourth predetermined value:
    determining that the corrective action is to increase the ratio to be greater than the fourth predetermined value; and
  if the ratio is greater than or equal to the fourth predetermined value:
    determining that the flow rate of the drilling fluid is less than the predetermined optimum flow rate; and
    determining that the corrective action is to increase the flow rate of the drilling fluid to be greater than or equal to the predetermined optimum flow rate.

7. The computer-implemented method of claim 1, further comprising:
  if the flow rate of the drilling fluid is greater than or equal to the predetermined optimum flow rate, determining whether the CCA is equal to the second predetermined value; and
  if the CCA is not equal to the second predetermined value, determining that the corrective action is to increase a rate of penetration of a drilling tool of the drilling system.

8. A non-transitory, computer-readable medium storing one or more instructions executable by a computer system to perform operations comprising:
  obtaining, in real-time from one or more sensors of a drilling system, real-time drilling data of a drilling operation of drilling a wellbore;
  using the real-time drilling data to calculate a carrying capacity index (CCI) of a drilling fluid and a cutting concentration in an annulus (CCA) of the wellbore;
  determining that at least one of the CCI and the CCA is outside a respective range;
  determining a corrective action to adjust the at least one of the CCI and the CCA to be within the respective range, wherein determining the corrective action comprises:
    (i) determining that the CCI is less than a first predetermined value, wherein the first predetermined value is an upper bound of the respective range of values for the CCI,
    (ii) determining that the CCA is less than or equal to a second predetermined value, wherein the second predetermined value is a lower bound of the respective range of values for the CCA,
    (iii) determining whether a transport ratio, TR, of the drilling fluid is greater than or equal to a third predetermined value,
    (iv) if the TR is less than the third predetermined value, determining that the corrective action is to increase the transport ratio to be greater than the third predetermined value, and
    (iv) if the TR is greater than or equal to the third predetermined value, determining whether a flow rate of the drilling fluid is greater than or equal to a predetermined optimum flow rate, and
      if the flow rate of the drilling fluid is less than the predetermined optimum flow rate, determining that the corrective action is to increase the flow rate of the drilling fluid to be greater than or equal to the predetermined optimum flow rate; and
  performing the corrective action, wherein performing the corrective action comprises controlling the drilling system to adjust one or more drilling parameters that affect the at least one of the CCI and the CCA.

9. The non-transitory, computer-readable medium of claim 8, wherein performing the corrective action comprises:
  displaying, via a graphical user interface (GUI), drilling instructions to perform one or more actions to adjust the at least one of the CCI and the CCA.

10. The non-transitory, computer-readable medium of claim 8, wherein determining corrective action to adjust the at least one of the CCI and the CCA to be within the respective range comprises:
  determining whether a ratio of a yield point (YP) of the drilling fluid to a plastic viscosity (PV) of the drilling fluid is greater than or equal to a fourth predetermined value;
  if the ratio is less than to the fourth predetermined value:
    determining that the corrective action is to increase the ratio to be greater than the fourth predetermined value; and
  if the ratio is greater than or equal to the fourth predetermined value:
    determining that the flow rate of the drilling fluid is less than the predetermined optimum flow rate; and
    determining that the corrective action is to increase the flow rate of the drilling fluid to be greater than or equal to the predetermined optimum flow rate.

11. The non-transitory, computer-readable medium of claim 8, further comprising:
  if the flow rate of the drilling fluid is greater than or equal to the predetermined optimum flow rate, determining whether the CCA is equal to the second predetermined value; and
  if the CCA is not equal to the second predetermined value, determining that the corrective action is to increase a rate of penetration of a drilling tool of the drilling system.

12. A computer-implemented system, comprising:
  one or more processors; and
  a non-transitory computer-readable storage medium coupled to the one or more processors and storing programming instructions for execution by the one or more processors, the programming instructions instructing the one or more processors to perform operations comprising:
    obtaining, in real-time from one or more sensors of a drilling system, real-time drilling data of a drilling operation of drilling a wellbore;
    using the real-time drilling data to calculate a carrying capacity index (CCI) of a drilling fluid and a cutting concentration in an annulus (CCA) of the wellbore;
    determining that at least one of the CCI and the CCA is outside a respective range;
    determining a corrective action to adjust the at least one of the CCI and the CCA to be within the respective range, wherein determining the corrective action comprises:
      (i) determining that the CCI is less than a first predetermined value, wherein the first predetermined value is an upper bound of the respective range of values for the CCI, (ii) determining that the CCA is less than or equal to a second predetermined value, wherein the second predetermined value is a lower bound of the respective range of values for the CCA, (iii) determining whether a transport ratio, TR, of the drilling fluid is greater than or equal to a third predetermined value, (iv) if the TR is less than the third predetermined value, determining that the corrective action is to increase the transport ratio to be greater than the third predetermined value, and (iv) if the TR is greater than or equal to the third predetermined value, determining whether a flow rate of the drilling fluid is greater than or equal to a predetermined optimum flow rate, and if the flow rate of the drilling fluid is less than the predetermined optimum flow rate, determining that the corrective action is to increase the flow rate of the drilling fluid to be greater than or equal to the predetermined optimum flow rate; and performing the corrective action, wherein performing the corrective action comprises controlling the drilling system to adjust one or more drilling parameters that affect the at least one of the CCI and the CCA.

13. The computer-implemented system of claim 12, wherein performing the corrective action comprises:

displaying, via a graphical user interface (GUI), drilling instructions to perform one or more actions to adjust the at least one of the CCI and the CCA.

\* \* \* \* \*